US009523654B2

United States Patent
Uemura et al.

(10) Patent No.: US 9,523,654 B2
(45) Date of Patent: Dec. 20, 2016

(54) AIR-FUEL RATIO DETECTION DEVICE

(71) Applicant: DENSO CORPORATION, Kariya, Aichi-pref. (JP)

(72) Inventors: Shinya Uemura, Obu (JP); Yusuke Shimizu, Chiryu (JP)

(73) Assignee: DENSO CORPORATION, Kariya (JP)

( * ) Notice: Subject to any disclaimer, the term of this patent is extended or adjusted under 35 U.S.C. 154(b) by 94 days.

(21) Appl. No.: 14/607,447

(22) Filed: Jan. 28, 2015

(65) Prior Publication Data

US 2015/0219590 A1 Aug. 6, 2015

(30) Foreign Application Priority Data

Feb. 5, 2014 (JP) .................................. 2014-20321

(51) Int. Cl.
*G01N 27/407* (2006.01)
*F02D 41/14* (2006.01)
*F02D 41/28* (2006.01)

(52) U.S. Cl.
CPC ......... *G01N 27/407* (2013.01); *F02D 41/1454* (2013.01); *F02D 41/28* (2013.01); *F02D 2041/286* (2013.01)

(58) Field of Classification Search
CPC F02D 41/1454; F02D 41/28; F02D 2041/286; G01N 27/407
USPC ............................................ 73/23.32, 23.31
See application file for complete search history.

(56) References Cited

U.S. PATENT DOCUMENTS

| 4,419,190 A | 12/1983 | Dietz et al. | |
|---|---|---|---|
| 6,468,478 B1 * | 10/2002 | Honda | G01N 27/4175 324/717 |
| 7,955,494 B2 * | 6/2011 | Kawase | G01N 27/4065 204/406 |
| 8,257,565 B2 * | 9/2012 | Kawase | G01N 27/4065 204/424 |
| 2005/0102334 A1 * | 5/2005 | Honda | F02D 41/28 708/202 |
| 2008/0197022 A1 * | 8/2008 | Suzuki | G01N 27/4175 205/775 |

FOREIGN PATENT DOCUMENTS

JP 2002-243694 A 8/2002

* cited by examiner

*Primary Examiner* — Michael A Lyons
*Assistant Examiner* — Suman K Nath
(74) *Attorney, Agent, or Firm* — Posz Law Group, PLC

(57) ABSTRACT

An air-fuel ratio detection device includes a resistor, a first voltage application section, a second voltage application section, an amplification section, an A/D conversion section, and an arithmetic section. The first voltage application section applies a direct current voltage to a first end of a series circuit constituted of an air-fuel ratio sensor and the resistor. The amplification section amplifies a voltage across the resistor and outputs an amplified voltage as an output voltage. The A/D conversion section carries out an A/D conversion of the output voltage every time before the second voltage application section switches a voltage applied to a second end of the series circuit between a first voltage and a second voltage. The arithmetic section calculates a sensor current and an impedance of the air-fuel ratio sensor using two consecutive A/D conversion results by the A/D conversion section.

8 Claims, 2 Drawing Sheets

AIR-FUEL RATIO DETECTION DEVICE

CROSS REFERENCE TO RELATED APPLICATIONS

The present application is based on and claims priority to Japanese Patent Application No. 2014-20321 filed on Feb. 5, 2014, the contents of which are incorporated in their entirety herein by reference.

TECHNICAL FIELD

The present disclosure relates to an air-fuel ratio detection device.

BACKGROUND

An air-fuel ratio detection device applying a voltage to an air-fuel ratio sensor and detecting electric current that flows in the air-fuel sensor as a sensor current depending on an air-fuel ratio has been known. As this kind of air-fuel ratio detection device, JP 57-187646 A (corresponding to U.S. Pat. No. 4,419,190 A) discloses an air-fuel ratio detection device including a detection resistor connected in series with an air-fuel ratio sensor and applying a direct current (DC) voltage and an alternating current (AC) voltage to a series circuit of the air-fuel ratio sensor and the current detection resistor.

In the air-fuel ratio detection device disclosed in JP 57-187646 A, a voltage across the current detection resistor is amplified by an amplifier, and an output of the amplifier is inputted into a low-pass filter and a high-pass filter. Then, an output of the low-pass filter is measured as a sensor current, and a value obtained by holding peak of an output of the high-pass filter by a peak-value rectifier is used as a value depending on a temperature of the air-fuel sensor (also depending on an impedance of the air-fuel sensor) for controlling a heat resistor (heater).

In the above-described technique, a DC component corresponding to the sensor current is extracted from the output of the amplifier (the voltage across the current detection resistor) by the low-pass filter, and the sensor current (eventually, the air-fuel ratio) is detected from the extracted DC component. In the above-described configuration, the output of the amplifier is converted into direct current by the low-pass filter, and an output change of the low-pass filter is slower than a change of the sensor current associated with a change of the air-fuel ratio. Thus, a detection responsiveness of the sensor current (eventually, a detection responsiveness of the air-fuel ratio) becomes low.

In addition, in the above-described technique, an AC component of amplitude depending on the impedance of the air-fuel ratio sensor is extracted by the high-pass filter. Because the low-pass filter and the high-pass filter are respectively provided for detecting the sensor current and the impedance of the air-fuel sensor, a size of the device increases.

SUMMARY

It is an object of the present disclosure to provide an air-fuel detection device that can increase a detection responsiveness of a sensor current of an air-fuel ratio sensor and can realize a downsize of the air-fuel detection device.

An air-fuel ratio detection device according to an aspect of the present disclosure includes a resistor for electric current detection, a first voltage application section, a second voltage application section, an amplification section, an A/D conversion section, and an arithmetic section. The resistor is connected in series with an air-fuel ratio sensor. The first voltage application section applies a direct current voltage to a first end of a series circuit constituted of the air-fuel ratio sensor and the resistor. The second voltage application section applies a voltage to a second end of the series circuit while alternately switching the voltage between a first voltage and a second voltage different from the direct current voltage at a predetermined period. The amplification section amplifies a voltage across the resistor and outputs an amplified voltage as an output voltage.

The A/D conversion section receives the output voltage of the amplification section as an input voltage and carries out an A/D conversion of the input voltage of the amplification section. The arithmetic section calculates a sensor current depending on an air-fuel ratio detected by the air-fuel ratio sensor and an impedance of the air-fuel ratio sensor from an A/D conversion result by the A/D conversion section.

The A/D conversion section carries out the A/D conversion every time before the second voltage application section switches the voltage applied to the second end of the series circuit. The arithmetic section calculates the sensor current and the impedance using two consecutive A/D conversion results by the A/D conversion section.

Because the air-fuel ratio detection device detects the sensor current without converting the output voltage of the amplification section into direct current using a low-pass filter, the air-fuel ratio detection device can increase a detection responsiveness of the sensor current. Thus, when the sensor current changes with a change of the air-fuel ratio, the sensor current after the change can be detected quickly. In addition, because the air-fuel ratio detection device does not need a low-pass filter for converting the output voltage of the amplification section into direct current and a high-pass filter for detecting an impedance of the air-fuel ratio sensor, the air-fuel ratio detection device can be downsized.

BRIEF DESCRIPTION OF THE DRAWINGS

Additional objects and advantages of the present disclosure will be more readily apparent from the following detailed description when taken together with the accompanying drawings. In the drawings.

DETAILED DESCRIPTION

Figure 1:
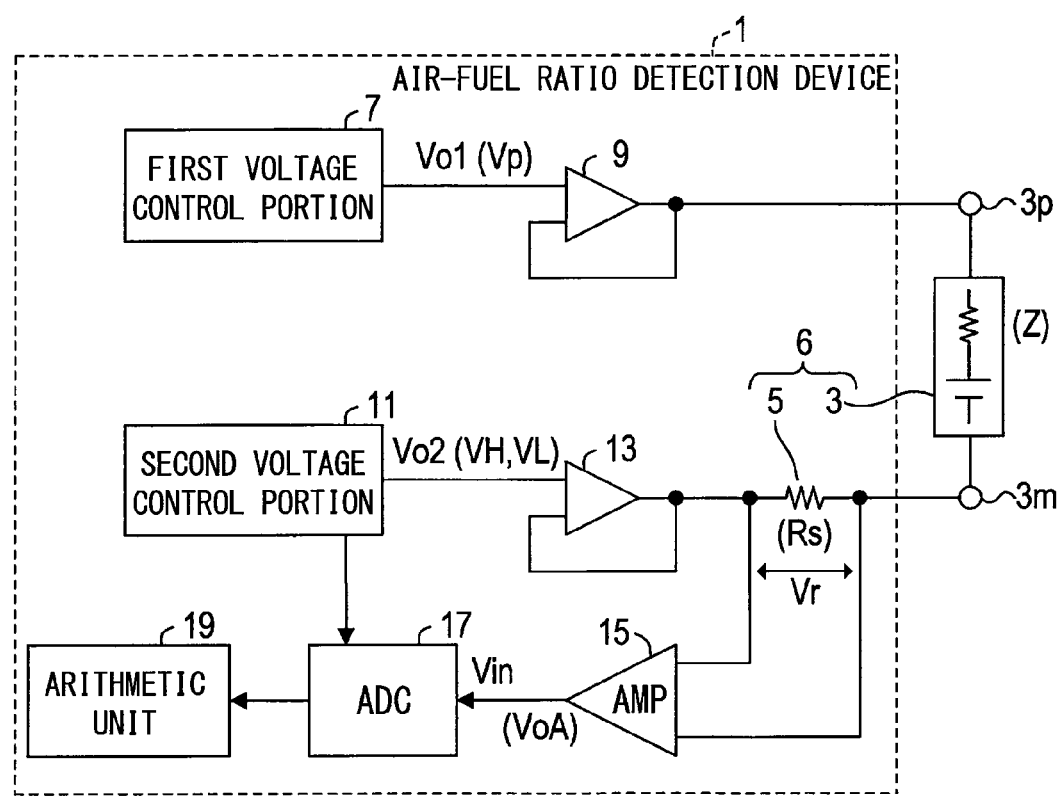
FIG. 1 a diagram illustrating a configuration of an air-fuel ratio detection device according to an embodiment of the present disclosure.

An air-fuel ratio detection device 1 according to an embodiment of the present disclosure will be described below. As illustrated in FIG. 1, the air-fuel ratio detection device 1 is connected with an air-fuel ratio sensor (hereafter simply referred to as a sensor) 3 for detecting an air-fuel ratio.

The sensor 3 is a limiting current air-fuel ratio sensor (so-called one cell limiting current laminated air-fuel ratio sensor) and is installed in an exhaust passage of a vehicle engine. When the sensor 3 is applied with a voltage, the sensor 3 generates a limiting current in accordance with an air-fuel ratio in exhaust gas. The limiting current becomes a sensor current depending on the air-fuel ratio detected by the sensor 3.

The air-fuel ratio detection device 1 includes a resistor 5 for electric current detection, a first voltage control portion 7, a buffer circuit 9, a second voltage control portion 11, and a buffer circuit 13. The resistor 5 is connected in series with the sensor 3. The first voltage control portion 7 and the buffer circuit 9 apply a DC voltage Vp to a first end of a series circuit 6 constituted of the sensor 3 and the resistor 5. The second voltage control portion 11 and the buffer circuit 13 applies a voltage to a second end of the series circuit 6 while alternately switching two kinds of voltages, that is, a first voltage VH and a second voltage VL, at a predetermined period Ts. In the present embodiment, the first voltage control portion 7 and the buffer circuit 9 correspond to a first voltage application section, and the second voltage control portion 11 and the buffer circuit 13 correspond to a second voltage application section.

Each of the buffer circuits 9, 13 is formed of an operational amplifier and outputs a voltage same as an received voltage from an output terminal. The buffer circuit 9 receives an output voltage Vo1 of the first voltage control portion 7, and the buffer circuit 13 receives an output voltage Vo2 of the second voltage control portion 11.

In the present embodiment, one end of the resistor 5 is connected to a minus side terminal 3m of the sensor 3. In addition, an output terminal of the buffer circuit 9 is connected to a plus side terminal 3p. The first voltage control portion 7 outputs a DC voltage Vp to the buffer circuit 9 as shown in a first stage in FIG. 2. Thus, the DC voltage Vp is applied from the buffer circuit 9 to the plus side terminal 3p of the sensor 3. In the present embodiment, the plus side terminal 3p of the sensor 3 corresponds to the first end of the series circuit 6. The DC voltage Vp may be fixed or may be changed in accordance with the sensor current.

An output terminal of the buffer circuit 13 is connected to the other end of the resistor 5 opposite to the sensor 3. The second voltage control portion 11 alternately switches the first voltage VH and the second voltage VL, which are different from the DC voltage Vp outputted from the first voltage control portion 7, at a predetermine period Ts and outputs the voltage as shown in a second stage in FIG. 2. In the period Ts, the output voltage Vo2 of the second voltage control portion 11 is the first voltage VH in a half of period Ts, and is the second voltage VL in the other half of period Ts. The first voltage VH and the second voltage VL switched as described above are applied from the buffer circuit 13 to the other end of the resistor 5. In the present embodiment, the DC voltage Vp, the first voltage VH, and the second voltage VL have a relationship of Vp>VH>VL. The other end of the resistor 5 corresponds to the second end of the series circuit 6.

For example, when the DC voltage Vp is 2.9 V, the first voltage VH is 2.7 V, and the second voltage VL is 2.3 V, an average value of the application voltage to the sensor 3 is 0.4 V (=2.9 V−(2.7 V+2.3 V)/2). A difference ΔV between the first voltage VH and the second voltage VL is 0.4 V (=2.7 V−2.3 V), and the difference ΔV becomes a change width that changes the application voltage to the sensor 3 in an AC manner. The application voltage to the sensor 3 is changed by the difference ΔV in the AC manner in order to detect the impedance (AC resistance) Z of the sensor 3.

As illustrated in FIG. 1, the air-fuel ratio detection device 1 further includes an amplification circuit (AMP) 15, an A/D converter (ADC) 17, and an arithmetic unit 19. The amplification circuit 15 amplifies the voltage Vr across the resistor 5 (see FIG. 2) and outputs an amplified voltage as an output voltage VoA. The A/D converter 17 receives the output voltage VoA as an input voltage Vin and carries out A/D conversion of the input voltage Vin. The arithmetic unit 19 calculates the sensor current Is depending on the air-fuel ratio detected by the sensor 3 and the impedance Z of the sensor 3 from the AD conversion result by the A/D converter 17.

Figure 2:
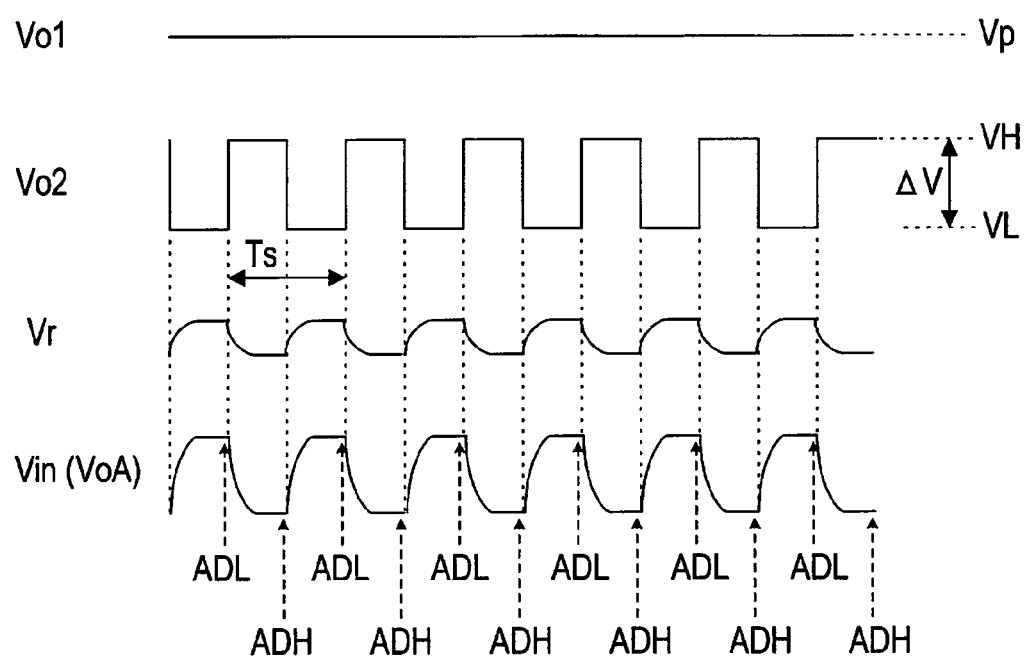
FIG. 2 is a diagram for explaining an operation of the air-fuel ratio detection device.

As illustrated in the second stage and the fourth stage in FIG. 2, the A/D converter 17 carries out the A/D conversion of the input voltage Vin from the amplification circuit 15 every time just before the second voltage control portion 11 switches the output voltage Vo2 (i.e., the voltage applied to the end of the series circuit 6) from one of the first voltage VH and the second voltage VL to the other.

In FIG. 2, upward dashed arrows indicate timings (A/D conversion timings) at which the A/D converter 17 carries out the A/D conversion of the input signal Vin. In addition, in FIG. 2 and the following description, "ADH" indicates the A/D conversion result at a time when the output voltage Vo2 of the second voltage is the first voltage VH. Specifically, "ADH" indicates the A/D conversion result just before the output voltage Vo2 is switched from the first voltage VH to the second voltage VL. In addition, in FIG. 2 and the following description, "ADL" indicates the A/D conversion result at a time when the output voltage Vo2 of the second voltage control portion 11 is the second voltage VL. Specifically, "ADL" indicates the A/D conversion result just before the output voltage Vo2 is switched from the second voltage VL to the first voltage VH. Furthermore, in "Vr" and "Vin (VoA)" in the third stage and the fourth stage in FIG. 2, in a direction of electric current that flows to the resistor 5, a direction from the sensor 3 to the buffer circuit 13 is set to be positive. The values of "Vr" and "Vin" increase with increase of the electric current in the positive direction. In addition, in FIG. 2, "Vr" and "Vin (VoA) change slowly compared with the change of the output voltage Vo2. This is because a signal line that transmits the output voltage Vo2 from the second voltage control portion 11 to the buffer circuit 13 and an input line to the amplification circuit 15 have capacity components, and the sensor 3 also has a capacity component.

The A/D converter 17 operates in synchronization with the second voltage control portion 11. The A/D converter 17 carries out the A/D conversion of the input voltage Vin at every timing of a predetermined time Ta before the second voltage control portion 11 switches the output voltage Vo. The predetermined time Ta is sufficiently shorter than the period Ts.

For example, the arithmetic unit 19 is formed of a microcomputer. The arithmetic unit 19 calculates the sensor current Is and the impedance Z of the sensor 3 using the two consecutive A/D conversion results by the A/D converter 17 (i.e., ADH and ADL of consecutive A/D conversion timings).

Specifically, the arithmetic unit 19 calculates the sensor current Is using Expression 1. In Expression 1, "G" indicates a gain (amplification degree) of the amplification circuit 15 and "Rs" indicates the resistance value of the resistor 5.

$$Is=(ADH+ADL)/2/G/Rs \qquad \text{Expression 1}$$

In other words, the arithmetic unit 19 calculates an average value of ADH and ADL at the consecutive A/D conversion timings and calculates the sensor current Is from the average value. Because the sensor current Is depends on the air-fuel ratio, it can also be said that the arithmetic unit 19 calculates the sensor current Is as the air-fuel ratio detected by the sensor 3. In an actual processing, the arithmetic unit 19 converts the calculated sensor current Is into the air-fuel ratio by applying the calculated sensor current Is to a predetermined expression or a data map. The process of converting the sensor current Is into the air-fuel ratio may also be carried out by a microcomputer other than the arithmetic unit 19.

In addition, the arithmetic unit 19 calculates the impedance Z of the sensor 3 using Expression 2.

$$Z=\{G \times \Delta V-(ADL-ADH)\} \times Rs/(ADL-ADH) \qquad \text{Expression 2.}$$

In other words, the arithmetic unit 19 calculates the impedance Z from a difference between ADH and ADL at consecutive A/D conversion timings.

In Expression 2, "$\Delta V$" indicates "VH−VL". Expression 2 is derived from Expressions 3, 4. In Expressions 2-4, in a manner similar to the third stage and the fourth stage in FIG. 2, in the direction of electric current that flows to the resistor 5, the direction from the sensor 3 to the buffer circuit 13 is set to be positive, and the output voltage VoA of the amplification circuit 15 increases with increase of the electric current in the positive direction.

$$ADH=G \times (Vp-VH) \times Rs/(Rs+Z) \qquad \text{Expression 3}$$

$$ADL=G \times (Vp-VL) \times Rs/(Rs+Z) \qquad \text{Expression 4}$$

The impedance Z of the sensor 3 is related to the temperature of the sensor 3. Thus, based on the calculated impedance Z, the arithmetic unit 19 determines whether the sensor 3 is in an active state or controls a heater (not shown) for heating the sensor 3.

The air-fuel ratio detection device 1 detects the sensor current Is without converting the output voltage VoA of the amplification circuit 15 into direct current using a low-pass filter. Thus, the air-fuel ratio detection device 1 can increase the detection responsiveness of the sensor current Is. In other words, when the sensor current Is changes with a change of the air-fuel ratio, the air-fuel ratio detection device 1 can immediately detect the sensor current Is after change. In addition, because the air-fuel ratio detection device 1 does not need a low-pass filter for converting the output voltage VoA of the amplification circuit 15 into direct current and a high-pass filter for detecting the impedance Z of the sensor 3, the air-fuel ratio detection device 1 can be downsized by decreasing the number of components.

The arithmetic unit 19 calculates an average value of consecutive ADH and ADL and calculates the sensor current Is from the average value. Thus, the arithmetic unit 19 can calculate the sensor current Is by a simple calculation. In addition, the calculated value of the sensor current Is can be updated twice a period Ts. Specifically, the calculated value of the sensor current Is can be updated at every half of the period Ts.

In addition, the arithmetic unit 19 calculates the impedance Z from the difference between the consecutive ADH and ADL (ADL−ADH or ADH−ADL). Thus, the arithmetic unit 19 can calculate the impedance Z with accuracy. Furthermore, the calculated value of the impedance Z can be updated twice a period Ts in a manner similar to the sensor current Is.

The A/D converter 17 carries out the A/D conversion every timing of the predetermined time Ta before the second voltage control portion 11 switches the voltage applied to the end of the series circuit 6. Thus, the A/D converter 17 can carry out the A/D conversion at timings appropriate for calculating the sensor current Is and the impedance Z.

Although one embodiment of the present disclosure has been described, it is to be noted that various changes and modifications will become apparent to those skilled in the art. The above-described values are mere examples and may be other values. For example, a time ratio of the first voltage VH and the second voltage VL in the period Ts may be a ratio other than 1:1. A DC voltage may be outputted from the buffer circuit 13, and a voltage outputted from the buffer circuit 9 may be alternately switched between the first voltage and the second voltage. The resistor 5 for electric current detection may be disposed on a current path between the plus side terminal 3p of the sensor 3 and the buffer circuit 9.

A function of one component in the above-described embodiment may be distributed as functions of a plurality of components, or functions of a plurality of components in the above-described embodiment may be integrated as a function of one component. At least a part of the configuration of the above-described embodiment may be replaced by a known configuration having a similar function. A part of the configuration of the above-described embodiment may be omitted as long as a technical problem can be solved.

Other than the air-fuel ratio detection device, the present disclosure can also be actualized by various aspects, such as a system that includes the air-fuel ratio detection device, a program that operates a computer as the air-fuel ratio detection device, a storage medium that stores the program, and a control method of an air-fuel ratio sensor.

What is claimed is:

1. An air-fuel ratio detection device comprising:
a resistor for electric current detection connected in series with an air-fuel ratio sensor;
a first voltage application section applying a direct current voltage to a first end of a series circuit constituted of the air-fuel ratio sensor and the resistor;
a second voltage application section applying a voltage to a second end of the series circuit while alternately switching the voltage between a first voltage and a second voltage different from the direct current voltage at a predetermined period;
an amplification section amplifying a voltage across the resistor and outputting an amplified voltage as an output voltage;
an A/D conversion section receiving the output voltage of the amplification section as an input voltage and carrying out an A/D conversion of the input voltage;
an arithmetic section calculating a sensor current depending on an air-fuel ratio detected by the air-fuel ratio sensor and an impedance of the air-fuel ratio sensor from an A/D conversion result by the A/D conversion section, wherein
the A/D conversion section carries out the A/D conversion every time before the second voltage application section switches the voltage applied to the second end of the series circuit, and
the arithmetic section calculates the sensor current and the impedance using two consecutive A/D conversion results by the A/D conversion section.

2. The air-fuel ratio detection device according to claim 1, wherein
the arithmetic section calculates an average value of the two consecutive A/D conversion results by the A/D conversion section, and calculates the sensor current from the average value.

3. The air-fuel ratio detection device according to claim 1, wherein
the arithmetic section calculates the impedance from a difference between the two consecutive A/D conversion results by the A/D conversion section.

4. The air-fuel ratio detection device according to claim 1, wherein the A/D conversion section carries out the A/D conversion a predetermined time before the second voltage application section switches the voltage applied to the second end of the series circuit.

5. The air-fuel ratio detection device according to claim 1, wherein
each of the first voltage and the second voltage is a positive voltage.

6. The air-fuel ratio detection device according to claim 1, wherein
the predetermined period in which the second voltage application section switches between the first voltage and the second voltage is a predetermined time period that occurs at a predetermined interval.

7. The air-fuel ratio detection device according to claim 6, wherein the predetermined interval is a predetermined, recurrent interval.

8. The air-fuel ratio detection device according to claim 6, wherein the first voltage is higher than the second voltage.

* * * * *